United States Patent [19]
Hart et al.

[11] Patent Number: 5,380,288
[45] Date of Patent: Jan. 10, 1995

[54] SURGICAL CANNULA AND TROCAR SYSTEM AND METHOD OF USING THE SAME

[75] Inventors: Rickey D. Hart, N. Attleboro; John T. Rice, Lincoln, both of Mass.

[73] Assignee: Innovasive Devices, Inc., Hopkinton, Mass.

[21] Appl. No.: 39,912

[22] Filed: Mar. 30, 1993

[51] Int. Cl.⁶ .............................................. A61B 17/34
[52] U.S. Cl. ..................... 604/167; 604/169; 606/185; 277/152
[58] Field of Search ............... 606/185; 604/167, 169, 604/164, 264, 174, 256; 277/152, 212 C

[56] References Cited

U.S. PATENT DOCUMENTS

| | | | |
|---|---|---|---|
| 4,240,411 | 12/1980 | Hosono | 604/167 X |
| 4,424,833 | 1/1984 | Spector et al. | 604/167 X |
| 4,535,773 | 8/1985 | Yoon | 128/630 X |
| 4,655,752 | 4/1987 | Honkanen et al. | 604/167 X |
| 4,929,235 | 5/1990 | Merry et al. | 604/167 |
| 4,950,257 | 8/1990 | Hibbs et al. | 604/167 X |
| 5,084,023 | 1/1992 | Lemieux | 604/164 X |
| 5,141,498 | 8/1992 | Christian | 604/167 |
| 5,154,701 | 10/1992 | Cheer et al. | 604/169 X |
| 5,226,426 | 7/1993 | Yoon | 604/169 X |

*Primary Examiner*—Michael H. Thaler
*Attorney, Agent, or Firm*—Pandiscio & Pandiscio

[57] ABSTRACT

An improved surgical cannula and trocar system for use in laparoscopic surgery. The system includes a novel surgical cannula including shield means for protecting operating room personnel from accidental contact with the trocar's sharp tip. The surgical cannula also includes improved sealing means for reliably preventing fluids from passing through the cannula both when an instrument extends through the cannula and no instrument extends through the cannula.

9 Claims, 9 Drawing Sheets

SURGICAL CANNULA AND TROCAR SYSTEM AND METHOD OF USING THE SAME

FIELD OF THE INVENTION

This invention relates to surgical instruments in general, and more particularly to surgical cannulas and surgical trocars.

BACKGROUND OF THE INVENTION

Surgical cannulas and surgical trocars are well known in the art.

Surgical cannulas are essentially tube-like members which are inserted into openings made in the body so as to line the openings and maintain them against closure. Surgical cannulas are used during so-called "closed" surgical procedures (e.g. laparoscopic procedures) to provide a portal between the region outside the body and the interior surgical site. In essence, the surgical cannulas serve as protective liners to allow surgical instruments to be inserted into, and withdrawn from, the internal surgical site with a minimum of trauma to the intervening tissue.

Surgical trocars are sharp, pointed instruments which are used to make openings in tissue so as to facilitate proper placement of the surgical cannulas in the body. More particularly, a surgical trocar is typically inserted into a cannula so that the trocar's sharp distal tip protrudes from the distal end of the cannula. The cannula and trocar are then advanced through the tissue as a unit, with the trocar's sharp tip leading the cannula so as to open up the tissue before the advancing cannula. Once the cannula has penetrated the tissue to the extent required, the trocar is withdrawn from the cannula. The cannula may thereafter be used to pass surgical instruments to and from the interior surgical site.

As noted above, when the trocar has been inserted into the cannula, the sharp distal tip of the trocar extends out of the distal end of the cannula. It will be appreciated, therefore, that this arrangement causes serious concerns among operating room personnel, since the sharp tip of the trocar is exposed and could cause injury to anyone accidentally coming into contact with the tip. This concern is heightened inasmuch as AIDS, hepatitis and/or other life-threatening disorders could be transferred from one person to another through such an injury. Thus, it is desirable to provide some sort of shield arrangement to protect operating room personnel from accidental contact with trocar's sharp point.

One such arrangement has been developed by United States Surgical Corp. ("USSC") of Norwalk, Conn. More particularly, USSC currently markets a surgical cannula and trocar system under the trade names "Auto Suture" and "SURGIPORT" wherein the trocar is provided with a telescoping sheath member which is capable of alternatively covering or exposing the trocar's sharp tip. Various locking arrangements are provided on the trocar which coact with counterpart elements on the surgical cannula to control sheath movement relative to the trocar's sharp tip.

Unfortunately, the foregoing surgical cannula and trocar system of USSC suffers from a number of disadvantages. Among other things, it requires that the surgical trocar be more complex in design. This increased complexity is undesirable, inasmuch as it leads to greater cost of manufacture and increased possibility of malfunction.

Furthermore, in laparoscopic procedures of the sort commonly used today, a plurality of surgical cannulas are typically inserted through the abdominal wall so that their distal ends reside inside the abdominal cavity while their proximal ends reside outside the body. In addition, in order to improve visual and instrument access to the interior surgical site, the patient's abdomen is typically inflated with a pressurized gas so as to extend the abdominal wall away from the interior organs. Inasmuch as the cannulas serve as a conduit between the pressurized surgical cavity and the region outside the body, some sort of sealing means must generally be provided with the surgical cannulas to prevent the pressurized gas from escaping out through the cannula, since this could cause the abdomen to deflate during the surgical procedure.

In this regard it should also be appreciated that the aforementioned sealing means must be effective both when an instrument extends through the cannula as well as when no instrument extends through the cannula. Furthermore, the sealing means must be capable of maintaining a good seal about an instrument even as the instrument is moved about during a surgical procedure. Unfortunately, the various sealing means heretofore provided on surgical cannulas have proven somewhat less than satisfactory, for a variety of different reasons.

OBJECTS OF THE PRESENT INVENTION

Accordingly, one object of the present invention is to provide a novel surgical cannula and trocar system which improves upon surgical cannula and trocar systems of the sort previously known in the art.

Another object of the present invention is to provide a novel surgical cannula and trocar system which provides shield means for protecting operating room personnel from accidental contact with the trocar's sharp tip, wherein the shield means is provided on the surgical cannula and not on the surgical trocar.

Still another object of the present invention is to provide a surgical cannula has which has improved sealing means, whereby fluids will be reliably prevented from passing through the cannula both when an instrument extends through the cannula and when no instrument extends through the cannula.

SUMMARY OF THE INVENTION

These and other objects are addressed by the present invention, which comprises a novel surgical cannula comprising an elongate housing, shield means, biasing means and sealing means.

The elongate housing has a longitudinal axis, a distal end and a proximal end. An axial passageway extends through the housing from the distal end to the proximal end.

The shield means comprises an elongate tubular sheath having a distal end and a proximal end. The sheath is slidably received in the housing's passageway so that the distal end of the sheath can project telescopically out of the distal end of the housing. The sheath is adapted to move between (1) a first position in which the distal end of the sheath projects out of the distal end of the housing, and (2) a second position in which the distal end of the sheath is withdrawn into the distal end of the housing.

The biasing means normally urges the sheath into the aforementioned first position. The biasing means may be overcome to permit the sheath to move into its aforementioned second position. The force applied by the biasing means to urge the sheath into its aforementioned first position is greater than forces of the type typically encountered in accidental contacts between operating room personnel and the surgical cannula. At the same time, however, the force applied by the biasing means to urge the sheath into its aforementioned first position is less than the axial force required to deploy a surgical cannula and trocar combination into tissue.

As a result of this construction, when an appropriate trocar is united with the surgical cannula so that the trocar's sharp distal point protrudes from the distal end of the housing, the trocar's point will normally reside within, and be shielded by, the distal end of the sheath. As a result, operating room personnel will be protected against accidental contact with the trocar's sharp point. At the same time, however, when the distal end of the cannula is deliberately forced against the patient's skin during cannula deployment, the distal end of the sheath will retract into the housing so as to expose the trocar's sharp point for tissue penetration.

The sealing means is adapted to selectively close off the cannula's axial passageway so as to prevent the passage of fluid through the passageway. At the same time, however, the sealing means-is also adapted to allow a surgical instrument to pass through the housing's passageway without compromising the cannula's fluid seal.

More particularly, the sealing means comprises a first sealing member, a second sealing member, and connecting means for connecting the first and second sealing members together in spaced relation to one another. The sealing means is disposed across the housing's passageway so that the first sealing member is disposed toward the distal end of the housing and the second sealing member is disposed toward the proximal end of the housing.

The first sealing member comprises a relatively thick layer of resilient material extending substantially completely across the housing's adjacent passageway. At least one slit extends axially through the first member so as to form a flap valve configuration.

The second sealing member comprises a relatively rigid elastomeric structure defining an axial opening and an outer edge. The second sealing member is sized so that it will not extend completely across the housing's adjacent passageway. By forming the second sealing member as a relatively rigid structure, the member's axial opening will tend to retain its shape.

The connecting means is formed of resilient material so that it is relatively easily deformable. The connecting means comprises a proximal portion connected to the periphery of the second sealing member and extending outboard thereof, and a side wall portion connected to the proximal portion and extending distally thereof so as to join the first sealing member. By forming the connecting means so that it is relatively easily deformable, the relatively rigid second sealing member can essentially "float" on the connecting means above the first sealing member. As a result, the second sealing member is able to move laterally and axially as necessary during cannula use.

The dimensions and relative elastic strengths of the second sealing member and the connecting means are selected so as to allow the shaft of a surgical instrument to be inserted axially through the second sealing member and make a close fit therewith, both when the surgical instrument is aligned with the housing's longitudinal axis and when the surgical instrument moves off the housing's longitudinal axis during instrument manipulation. In particular, by forming the second sealing member so that it behaves as a relatively rigid elastomeric structure (such that its axial opening tends to retain its shape) and by forming the connecting means so that it is relatively easily deformable (such that the relatively rigid second sealing member can essentially "float" on the connecting means above the first sealing member), the second sealing member will be able to establish a close seal about the surgical instrument and then maintain that close seal even as the surgical instrument moves laterally within the cannula during instrument manipulation.

BRIEF DESCRIPTION OF THE DRAWINGS

Still other objects and features of the present invention will be more fully disclosed or rendered obvious by the following detailed description of the preferred embodiment of the invention, which is to be considered together with the accompanying drawings wherein like numbers refer to like parts and further wherein.

DETAILED DESCRIPTION OF THE PREFERRED EMBODIMENT

Looking first at FIGS. 1-9, the preferred embodiment of the present invention comprises a surgical cannula 5 generally comprising an elongate housing 100, shield means 200, biasing means 300 and sealing means 400.

Figure 1:
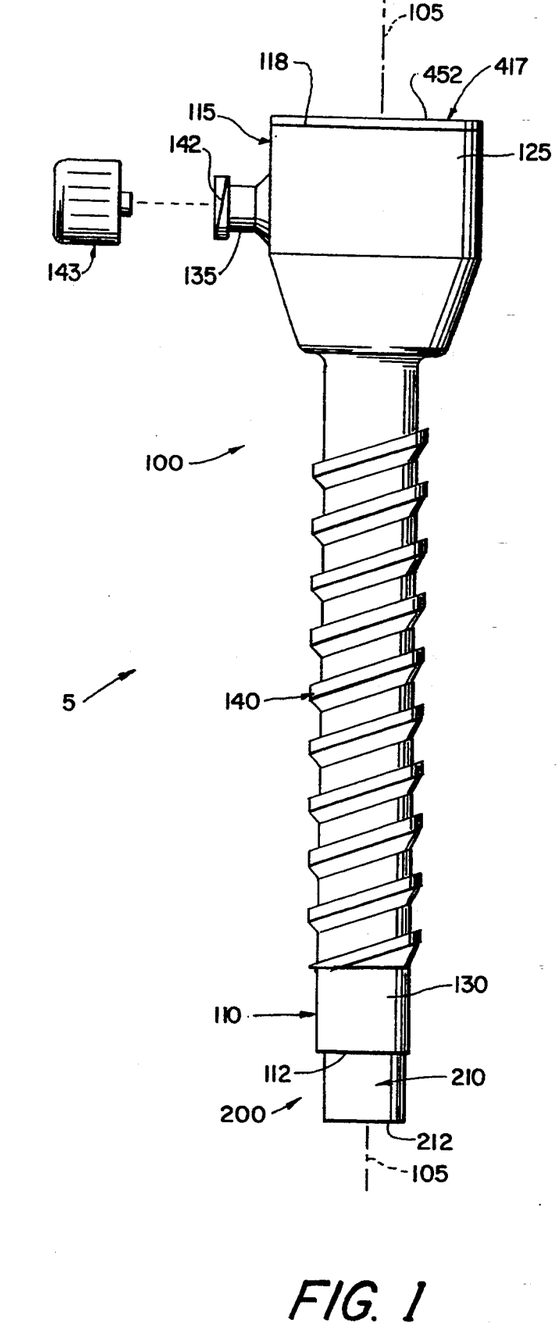
FIG. 1 is a side view of a surgical cannula made in accordance with the present invention, with the cannula's sheath being disposed in its aforementioned first position in which the distal end of the sheath projects out of the distal end of the housing.
Figure 2:
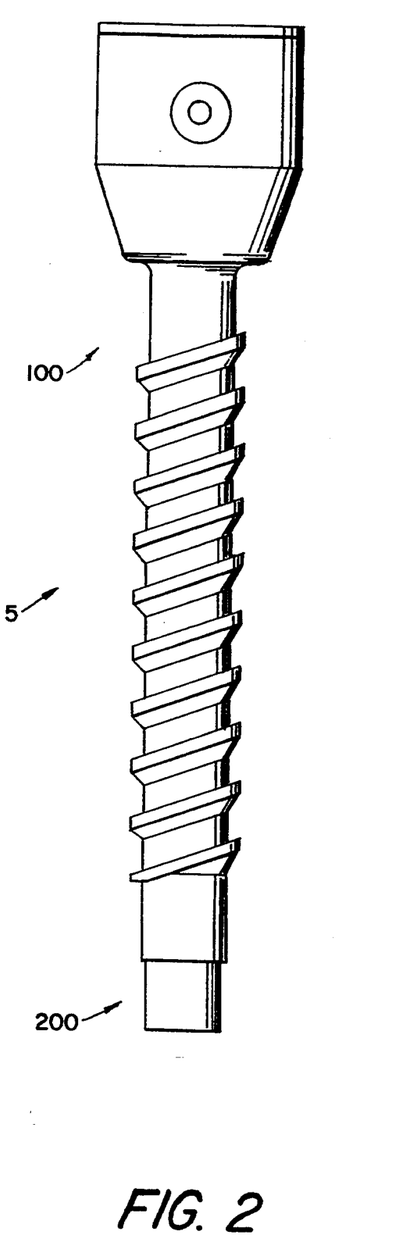
FIG. 2 is a view like that of FIG. 1, with the surgical cannula having been rotated 90° about its longitudinal axis and with the cannula's side extension cap having been omitted from the drawing (and as it has been omitted from FIGS. 3-6, 9, 16 and 18)
Figure 3:
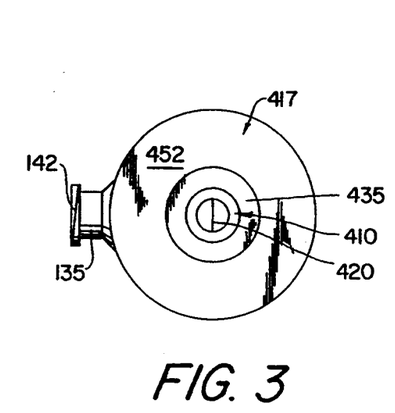
FIG. 3 is a top view of the same surgical cannula.
Figure 4:
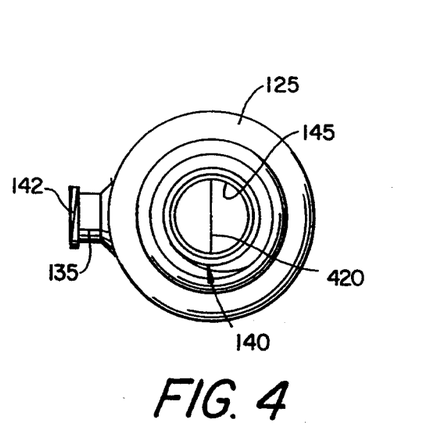
FIG. 4 is a bottom view of the same surgical cannula.
Figure 5:
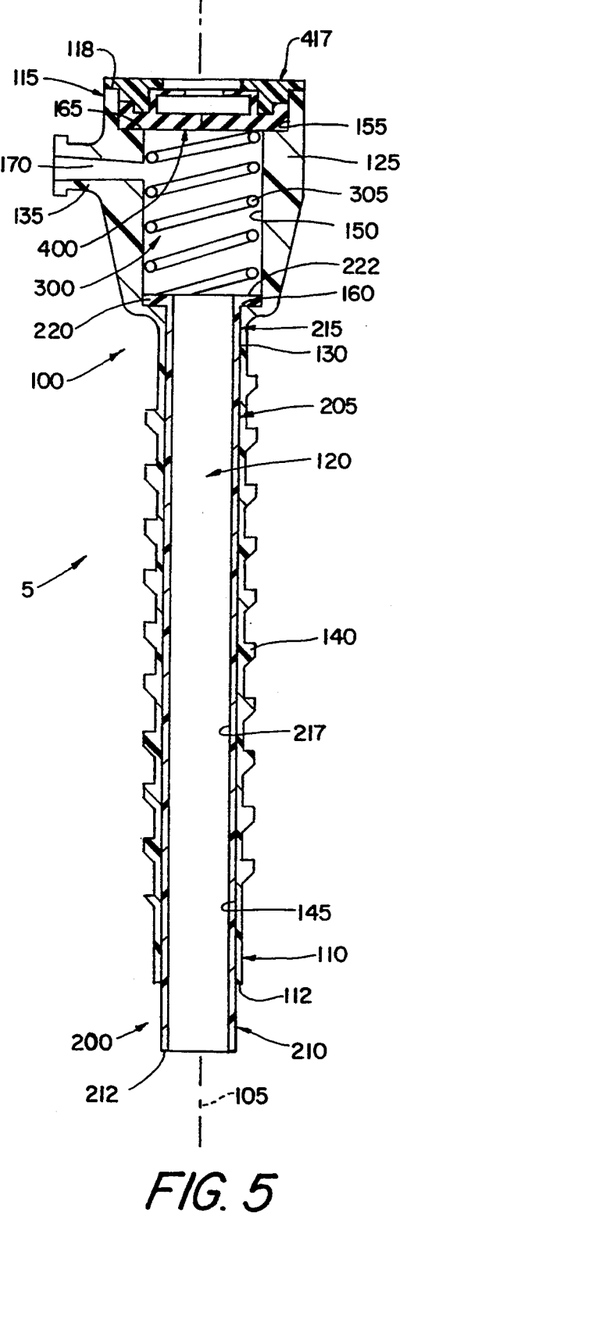
FIG. 5 is a side view in section of the same surgical cannula.

Elongate housing 100 comprises a longitudinal axis 105, a distal end 110 terminating in a distal end surface 112, and a proximal end 115 terminating in a proximal end surface 118. An axial passageway 120 extends through the housing from distal end 110 to proximal end 115, opening on both distal end surface 112 and proximal end surface 118.

More particularly, housing 100 has an expanded upper section 125, a reduced lower section 130, and a side extension 135. Upper section 125, lower section 130 and side extension 135 are all formed integral with one another, preferably from a selected rigid or semi-rigid plastic material. The housing's reduced lower section 130 is formed so that it has a helical screw thread 140 disposed on its outer surface along the majority of its length. The housing's side extension 135 has a relatively short helical screw thread 142 disposed on its outer surface along the outboard portion of the side extension. A side extension cap 143 (FIG. 1) is adapted to screw onto threads 142 so as to close off side extension 135, as will hereinafter be described in further detail.

A bore 145 and a pair of counterbores 150 and 155 extend through housing 100 along the housing's longitudinal axis 105. Bore 145, counterbore 150 and counterbore 155 together constitute the aforementioned passageway 120. More particularly, the distal end of bore 145 opens on the housing's distal end surface 112, the distal end of counterbore 150 communicates with the proximal end of bore 145, the distal end of counterbore 155 communicates with the proximal end of counterbore 150, and the proximal end of counterbore 155 opens on the housing's proximal end surface 118. An annular shoulder 160 is formed at the intersection of bore 145 and counterbore 150, and another annular shoulder 165 is formed at the intersection of counterbore 150 and counterbore 155.

Another bore 170 extends along side extension 135 and intersects counterbore 150 as shown. Side bore 170 may or may not be tapered inwardly along its length if desired. Bore 170 is closed off by side extension cap 143 when side extension cap 143 is screwed onto side extension 135.

Figure 9:
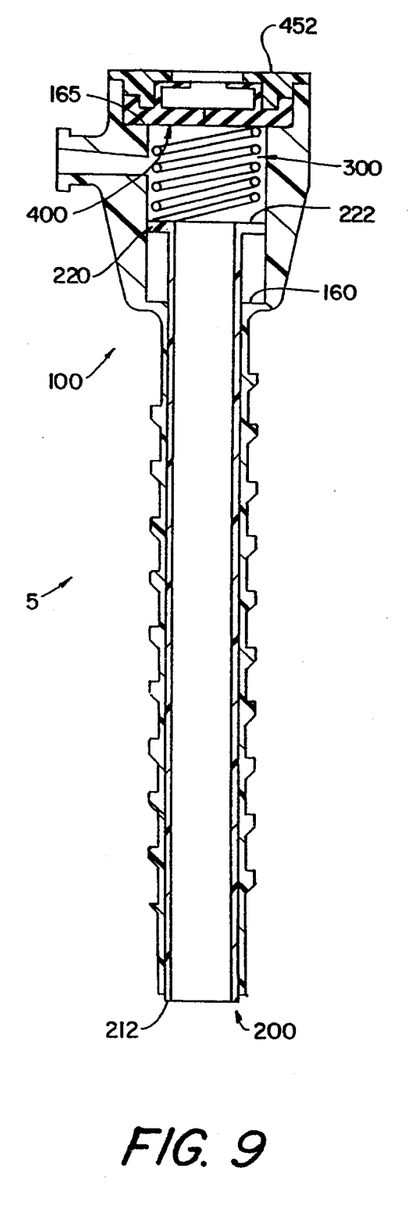
FIG. 9 is a view like that of FIG. 5, except that the cannula's sheath is disposed in its aforementioned second position in which the distal end of the sheath is withdrawn into the distal end of the housing.

Shield means 200 comprises an elongate tubular sheath 205 having a distal end 210 terminating in a distal end surface 212 and a proximal end 215. A central passageway 217 extends through sheath 205 from its distal end 210 to its proximal end 215. Sheath 205 is slidably received in the housing's passageway 120 so that the sheath's distal end 210 can project telescopically out of the housing's distal end 110. Sheath 205 is adapted to move between (1) a first position in which the sheath's distal end 210 projects out of the housing's distal end 110 (FIGS. 1, 2 and 5), and (2) a second position in which the sheath's distal end 210 is withdrawn into the housing's distal end 110 (FIG. 9). It is to be appreciated that when sheath 205 is in its aforementioned second position, the sheath's distal end surface 212 will be approximately aligned with the housing's distal end surface 112, in the manner shown in FIG. 9.

More particularly, the body of sheath 205 is sized so as to make a close sliding fit within the housing bore 145. Sheath 205 also includes an annular flange 220 at its proximal end 215. Flange 220 is in turn sized so as to make a close sliding fit within the housing's counterbore 150. Flange 220 terminates in a flange end surface 222. Sheath 205 is sized so that when its flange 220 engages the housing's annular shoulder 160, the sheath's distal end 210 will extend sufficiently far beyond the distal end of the housing as to be able to cover the sharp tip of a trocar inserted in the cannula, as will hereinafter be described in further detail. At the same time, sheath 205 is sized so that when its distal end 210 has been withdrawn into the housing's distal end, with the sheath's distal end surface 212 approximately aligned with the housing's distal end surface 112, the sheath's flange 220 will reside approximately midway along the housing's counterbore 150 (FIG. 9).

Biasing means 300 comprises a compression spring 305. Spring 305 is sized to fit within counterbore 150, captured between end surface 222 of sheath flange 220 and sealing means 400. Spring 305 normally urges sheath 205 into its aforementioned first position, in which the sheath's flange 220 engages the housing's annular shoulder 160 and the sheath's distal end 210 projects out of the housing's distal end 110. Spring 305 may be overcome to permit sheath 205 to move into its aforementioned second position, in which the sheath's distal end 210 is withdrawn into the housing's distal end 110, with the sheath's distal end surface 212 being approximately aligned with the housing's distal end surface 112. Spring 305 is chosen so that the force applied by the spring to urge sheath 205 into its aforementioned first position is greater than forces of the type typically encountered in accidental contacts between operating room personnel and the surgical cannula. As a result, sheath 205 will not retract into housing 100 due to such accidental contacts. At the same time, however, spring 305 is chosen so that the force applied by the spring to urge sheath 205 into its aforementioned first position is less than the axial force required to deploy a surgical cannula and trocar combination into tissue. As a result, sheath 205 will retract into housing 100 during deliberate cannula deployment.

As a result of this construction, and as will hereinafter be discussed in further detail, when an appropriate trocar is inserted into the surgical cannula so that the trocar's sharp distal point protrudes from the distal end of housing 100, the trocar's point will normally reside within, and be shielded by, the distal end of the sheath. As a result, operating room personnel will be protected against accidental contact with the trocar's sharp point. At the same time, however, when the distal end of the cannula is deliberately forced against the patient's skin during cannula deployment, the distal end of the sheath will retreat into the housing so as to expose the trocar's sharp point for tissue penetration.

Sealing means 400 is adapted to selectively close off the housing's passageway 120 so as to prevent the passage of fluid through the passageway. At the same time, sealing means 400 is also adapted to allow a surgical instrument to pass through the housing's passageway without compromising the cannula's fluid seal, as will hereinafter be described in further detail.

Figure 7:
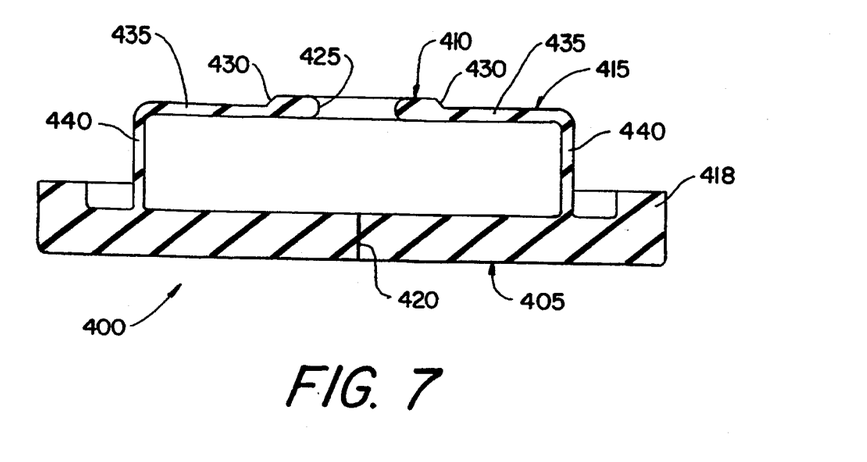
FIG. 7 is a side view in section of the sealing means utilized in the surgical cannula shown in FIGS. 1-6.
Figure 8:
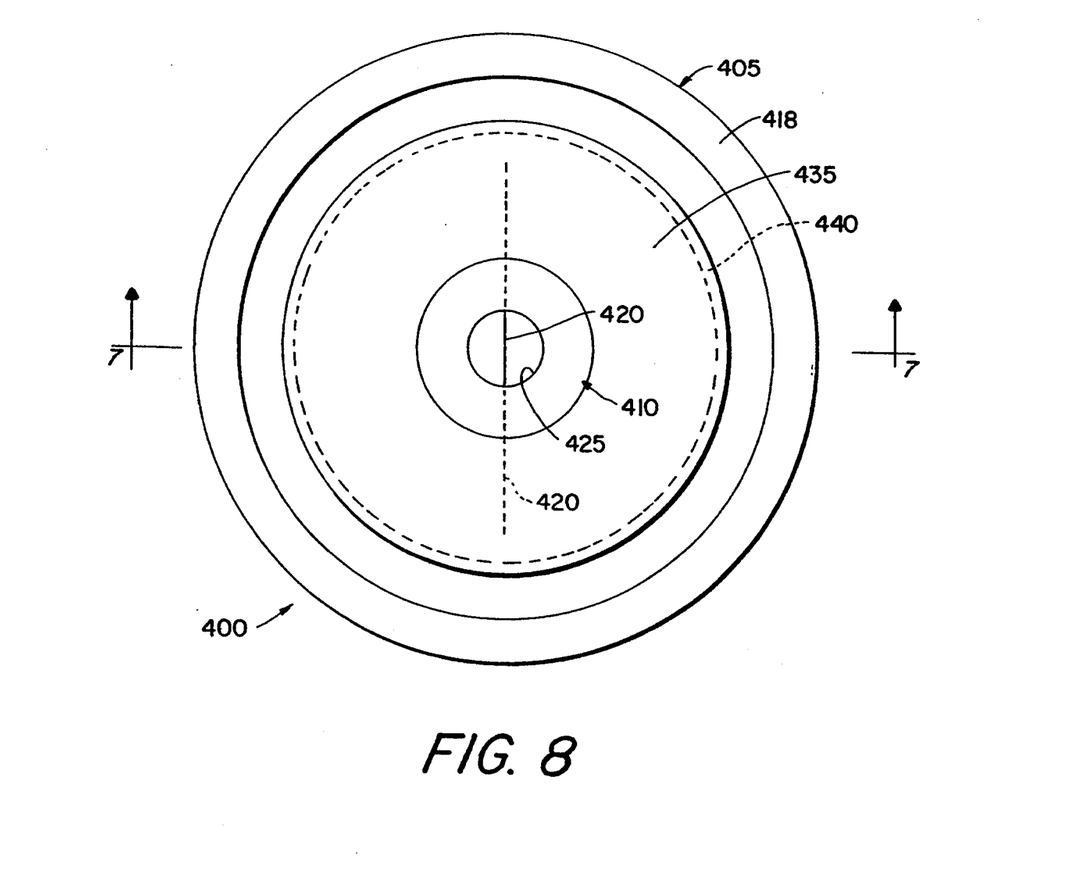
FIG. 8 is a top view of the sealing means shown in FIG. 7.

More particularly, sealing means 400 comprises a first sealing member 405, a second sealing member 410, and connecting means 415 connecting the first and second sealing members together in spaced relation to one another. First sealing member 405, second sealing member 410 and connecting means 415 are preferably all formed integral with one another, out of an appropriate resilient material. By way of example, it has been found that Dow Corning's silicone rubber (trade designation #1125 U) may be used. Sealing means 400 is disposed across the housing's passageway 120 so that first sealing member 405 is disposed toward the distal end of housing 100 and second sealing member 410 is disposed toward the proximal end of housing 100. A cap member 417 holds sealing means 400 in place, as will hereinafter be described in further detail.

Figure 18:
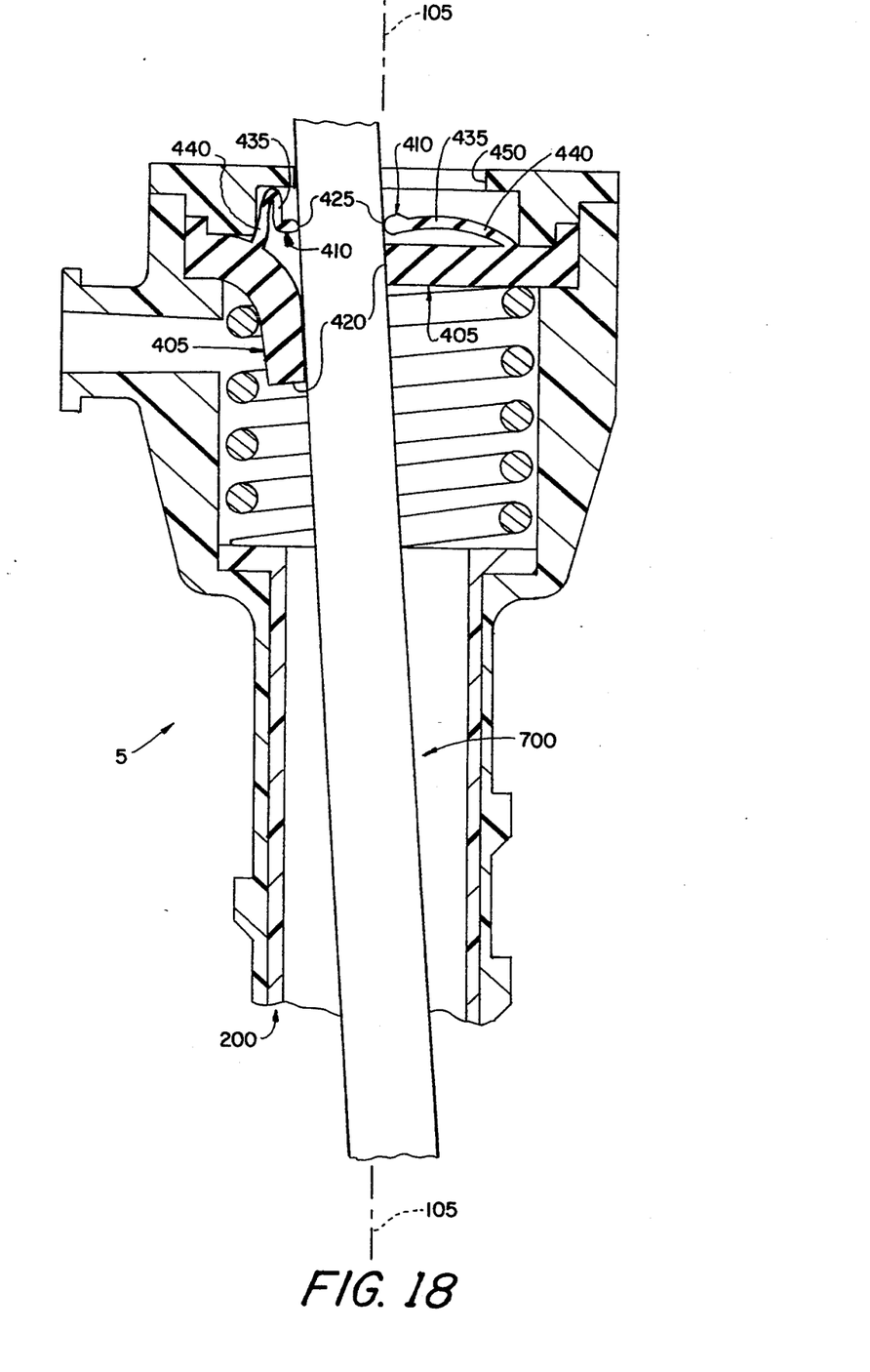

First sealing member 405 comprises a relatively thick layer of resilient material sized to extend completely across the housing's counterbore 155. Preferably an upraised annular rim 418 is disposed about the periphery of first sealing member 405. At least one slit 420 extends axially through first member 405 so as to form a flap valve configuration. It is to be appreciated that first sealing member 405 is formed with a sufficient thickness and durometer such that slit 420 will normally remain closed (and hence member 405 impervious to fluid flow) when no surgical instrument is extending through cannula 5, in the manner shown in FIG. 6. By way of example, when first sealing member 405 is formed out of Dow Corning's #1125 U silicone rubber, member 405 preferably has an axial thickness of about 0.095 inches. At the same time, first seal member 405 is adapted to yield about its slit 420 so as to permit a surgical instrument to extend through first seal member 405, in the manner shown in FIGS. 16 and 18, as will hereinafter be described in further detail.

Second sealing member 410 comprises a relatively rigid elastomeric structure defining an axial opening 425 and an inclined outer edge 430. Axial opening 425 is sized to make a close fit with a surgical instrument extending through cannula 5. The second sealing member's inclined outer edge 430 is preferably inclined at an angle of approximately 45°, although other angles may also be used. Second sealing member 410 is sized so that its diameter is significantly less than the diameter of counterbore 155. By way of example, in the case when counterbore 155 has a diameter of approximately 0.855 inches, second sealing member 410 might have a diameter (as taken at the outermost points on its inclined outer edge 430) of approximately 0.260 inches. It is to be appreciated that second sealing member 410 is formed with a sufficient thickness and durometer that second sealing member 410 will behave as a relatively rigid elastomeric structure during cannula use. By way of example, when second sealing member 410 is formed out of Dow Corning's #1125 U silicone rubber, member 410 preferably has an axial thickness of approximately 0.060 inches. By forming second sealing member 410 as a relatively rigid elastomeric structure, the member's axial opening 425 will tend to retain its shape. At the same time, however, second sealing member 410 has sufficient resiliency that its axial opening 425 can be enlarged slightly so as to receive and form a close seal about an instrument extending therethrough. Axial opening 425 is sized so as to normally have a diameter slightly smaller than the diameter of a surgical instrument to be inserted through the cannula, in order that second sealing member 410 will have to yield slightly to accommodate that instrument.

Connecting means 415 connects first sealing member 405 to second sealing member 410. Connecting means 415 is formed so that it is relatively easily deformable, in order that the relatively rigid second sealing member 410 can essentially "float" above first sealing member 405. As a result, second sealing member 410 is able to move laterally and axially as necessary during use. More particularly, connecting means 415 comprises a proximal portion 435 connected to the periphery of second sealing member 410 and extending outboard thereof, and a side wall portion 440 connected to the periphery of proximal portion 435 and extending distally thereof so as to join first seal member 405. Proximal portion 435 is sized so that the outermost surfaces of side wall portion 440 will lie inboard of, and spaced from, annular rim 418. In addition, the size and construction of proximal portion 435 and side wall portion 440 are coordinated so that these two portions are easily deformable. By way of example, in the case where proximal portion 435 and side wall portion 440 are formed out of Dow Corning's #1125 U silicone rubber, proximal portion 435 and side wall portion might have a thickness of approximately 0.015 inches, so as to ensure that these two members are easily deformable.

The dimensions and relative elasticity of second sealing member 410 and connecting means 415 are selected so as to allow second sealing member 410 to make a close fit with the shaft of a surgical instrument inserted through axial opening 425, and to maintain this close fit even when the surgical instrument moves off the housing's longitudinal axis during instrument manipulation.

More particularly, by sizing the diameter of the second sealing member's axial opening 425 slightly smaller than the diameter of a surgical instrument which is to be passed through the surgical cannula, second sealing member 410 will make a close fit about the instrument as it is inserted axially through second sealing member 410. At the same time, however, by forming second sealing member 410 as a comparatively rigid structure relative to connecting means 415, connecting means 415 will permit the second sealing member 410 to "float" laterally and axially on the connecting means as needed to accommodate movement of the surgical instrument off the housing's longitudinal axis 105 during instrument manipulation. As second sealing member 410 "floats" on connecting means 415, substantially no deformation of axial opening 425 will take place, thereby assuring a secure seal with the surgical instrument.

Figure 6:
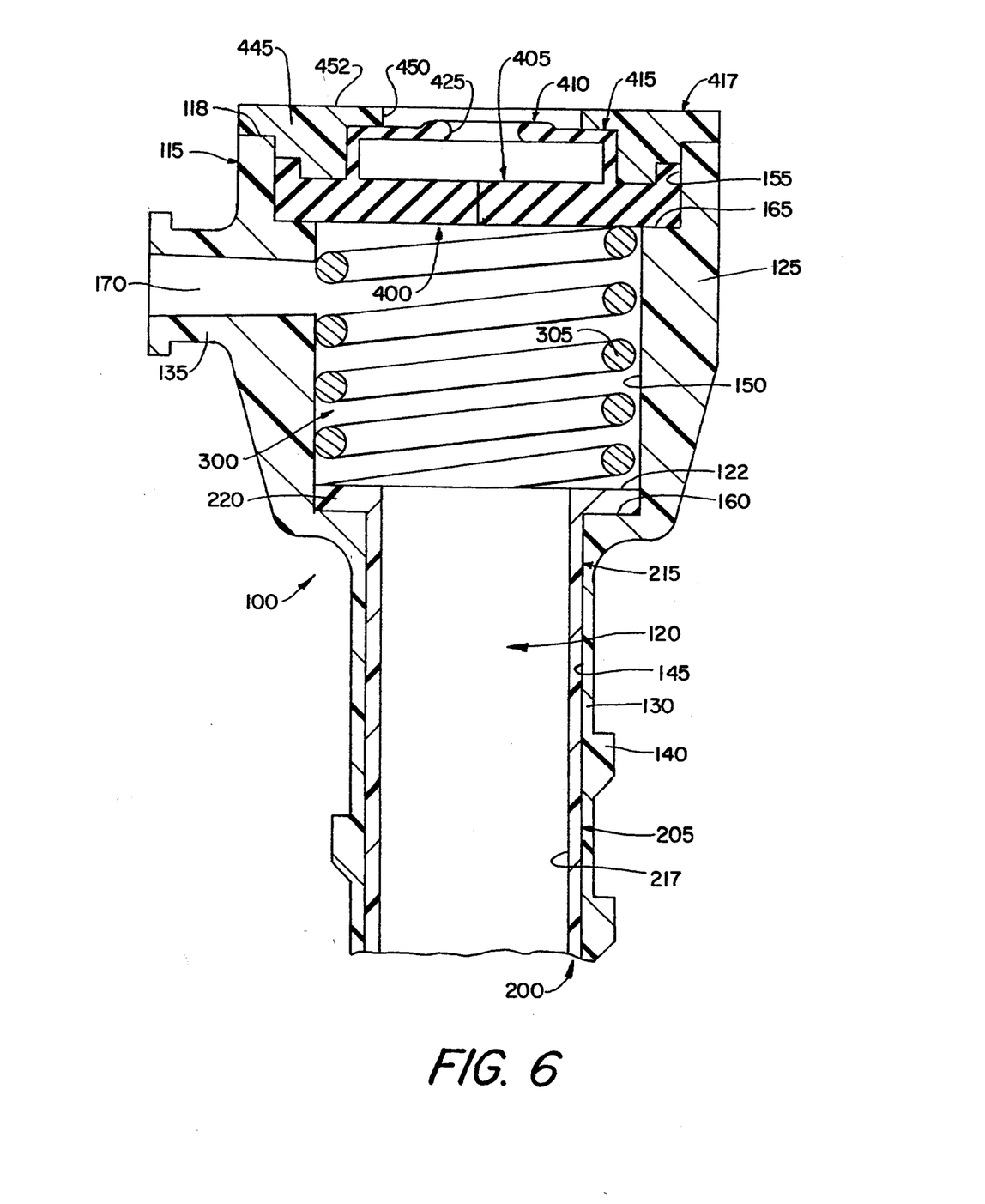
FIG. 6 is an enlarged side view in section showing the proximal end of the same surgical cannula.

Cap 417 is provided to hold sealing means 400 in housing 100. Cap 417 includes an axial projection 445, a central opening 450, and a top surface 452. Axial projection 445 has a stepped profile in order that projection 445 can engage and hold sealing means 400 compressed securely against housing shoulder 165 when cap 417 engages housing proximal end surface 118. Central opening 450 has a diameter significantly larger than the diameter of the seal's axial opening 425, whereby a surgical instrument may be easily introduced into axial opening 425. At the same time, the cap's central opening 450 has a diameter less than the diameter of the seal's side wall portion 440, in order that the cap will overlie at least a portion of the seal's proximal portion 435. When cap 417 is united with housing 100 (e.g. by friction fit, gluing, sonic welding, etc.), the cap's top surface 452 will form the proximal end surface for the complete surgical cannula 5.

Figure 10:
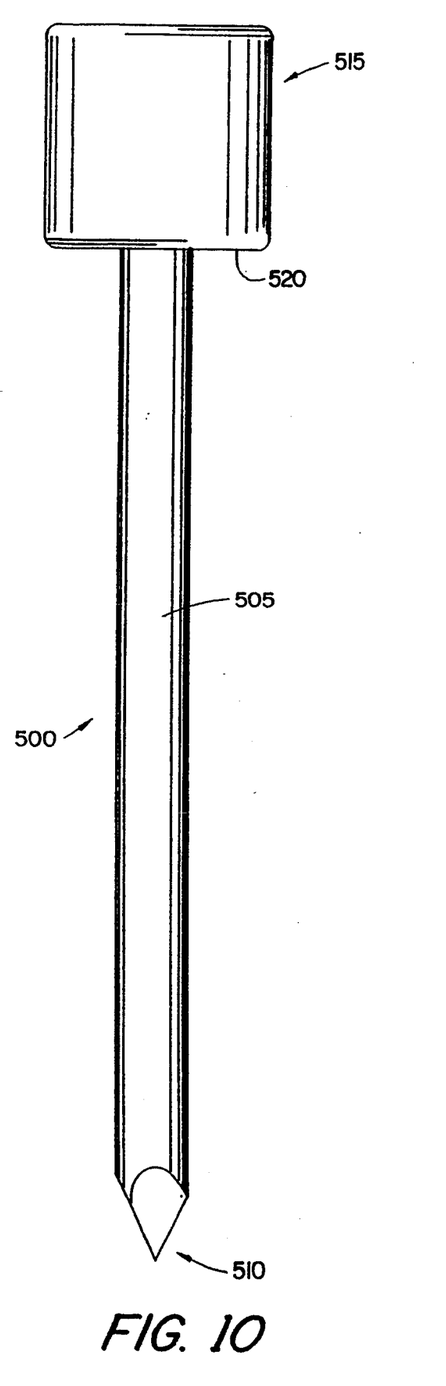
FIG. 10 is a side view of a surgical trocar to be used in conjunction with the surgical cannula shown in the drawings.

Looking next at FIG. 10, cannula 5 is intended to be used in conjunction with a surgical trocar such as the surgical trocar 500 shown. Trocar 500 generally comprises a shaft 505 having a sharp, typically triangular point 510 at its distal end and a handle 515 at its proximal end. Handle 515 has an end surface 520 on its distal side. The various dimensions of trocar 500 are coordinated with the various dimensions of surgical cannula 5 so that the trocar may be properly used in conjunction with the cannula. More particularly, shaft 505 is formed with a diameter slightly less than the diameter of the sheath's central passageway 217, in order that the trocar can make a close sliding fit within the cannula. In addition, trocar 500 is formed so that the distance between its handle surface 520 and the distalmost point on its tip 510 is less than the distance between the sheath's distal end surface 212 and the cannula's proximalmost surface 452 when the sheath is in its aforementioned first position, but more than the distance between the sheath's distal end surface 212 and the cannula's proximalmost surface 452 when the sheath is in its aforementioned second position. As a result of this construction, when trocar 500 is inserted into cannula 5 so that the trocar's surface 520 engages the cannula's proximal end surface 452, the trocar's sharp distal tip 510 will normally reside within, and be shielded by, the extended distal end of the sheath and operating room personnel will be protected from accidental contact with the trocar's sharp point. At the same time, however, when the distal end of the cannula is deliberately forced against the patient's skin during cannula deployment, the distal end of the sheath can retreat into the cannula's housing and the sharp tip of the trocar will be exposed for tissue penetration.

The surgical cannula and trocar combination is intended to be used as follows.

Figure 11:
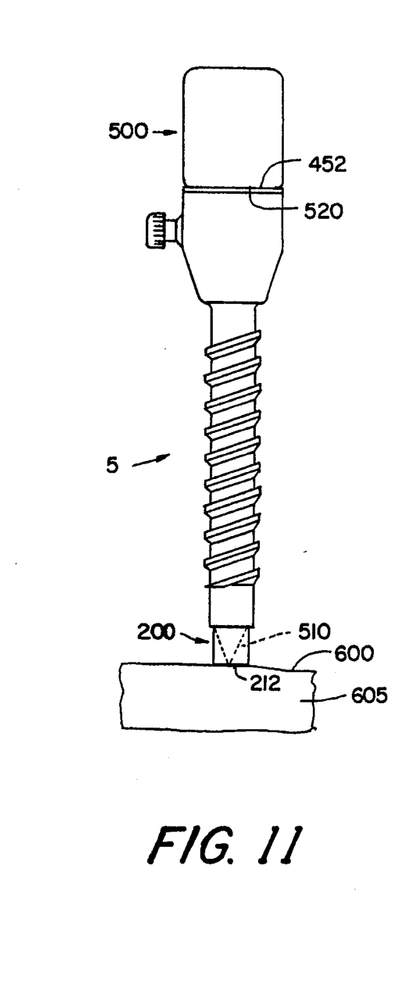
FIGS. 11-13 show the surgical cannula and surgical trocar being deployed as a unit through the abdominal wall of a patient.

Looking first at FIG. 11, trocar 500 is initially inserted into cannula 5 so that the trocar's handle surface 520 engages the cannula's cap surface 452, with the trocar's shaft 505 extending through the cap's central opening 450, the second sealing member's axial opening 425, the first sealing member's slit 420, the interior of compression spring 305 and the passageway 217 formed in sheath 205. It will be appreciated that as the trocar's shaft 505 passes through the second sealing member's axial opening 425, second sealing member 410 will give to accommodate and make a close fit around the relatively large diameter trocar. Furthermore, it will be appreciated that as the trocar's shaft 505 passes through the first sealing member's slit 420, the first sealing member 405 will flap open in a distal direction about its slit 420 so as to allow the shaft to pass. At this point sheath 205 will normally be held in its aforementioned first position by compression spring 305, so that the distal end of the sheath will project out of the distal end of the cannula and thereby shield the trocar's sharp distal tip 510. It will be appreciated that when the cannula and trocar combination is in this position, it can be safely handled by operating room personnel without fear of accidental injury from the trocar's sharp tip 510.

Figure 12:
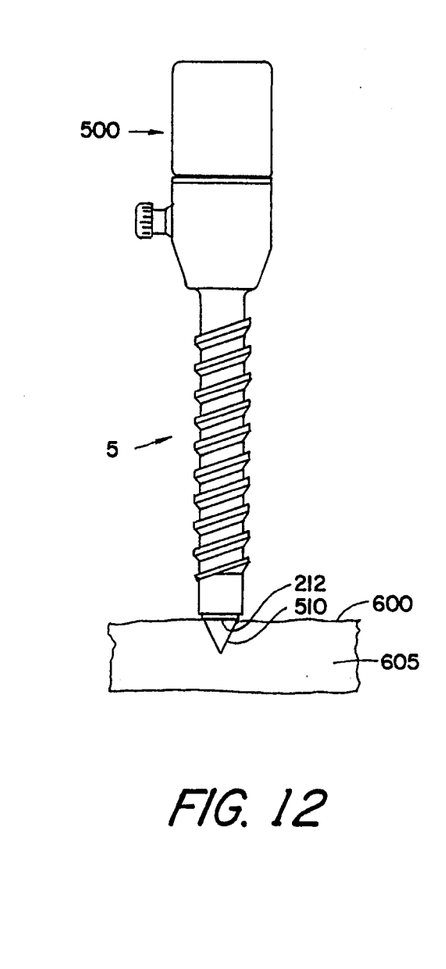

When desired, the cannula and trocar combination can be safely brought down into contact with the outer surface 600 of the patient's abdominal wall 605, with the sheath's distal end surface 212 lightly contacting skin surface 600. At this point the trocar's sharp tip 510 will, of course, still be spaced from skin surface 600. Next, the cannula and trocar combination is forced against the patient's abdominal wall 605. This causes the cannula's sheath 205 to gradually retract into the cannula's housing so as to expose the trocar's sharp point 510 for tissue penetration, in the manner shown in FIG. 12. It will be appreciated that in FIG. 12 sheath 205 is shown fully retracted into its aforementioned second position.

Figure 13:
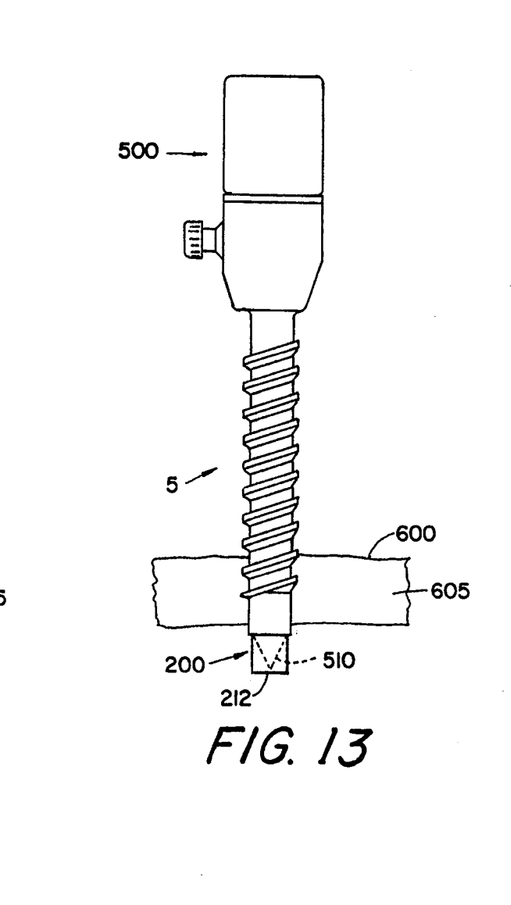

With the trocar's sharp tip 510 leading the way, the cannula and trocar combination can be pushed all the way through the abdominal wall 605, until the distal portions of the trocar and cannula enter the abdominal cavity. It will be appreciated that as soon as the sheath's distal end surface 212 passes completely through abdominal wall 605, spring 305 will cause sheath 205 to return to its aforementioned first position, whereupon it will once again cover the trocar's sharp distal tip 510. This will help protect the patient's internal organs from any accidental contact with the trocar's sharp tip. See FIG. 13. As shown in FIG. 13, the cannula's helical screw threads 140 are preferably in engagement with the patient's abdominal wall 605 when the distal portions of the trocar and sheath enter the abdominal cavity.

Figure 14:
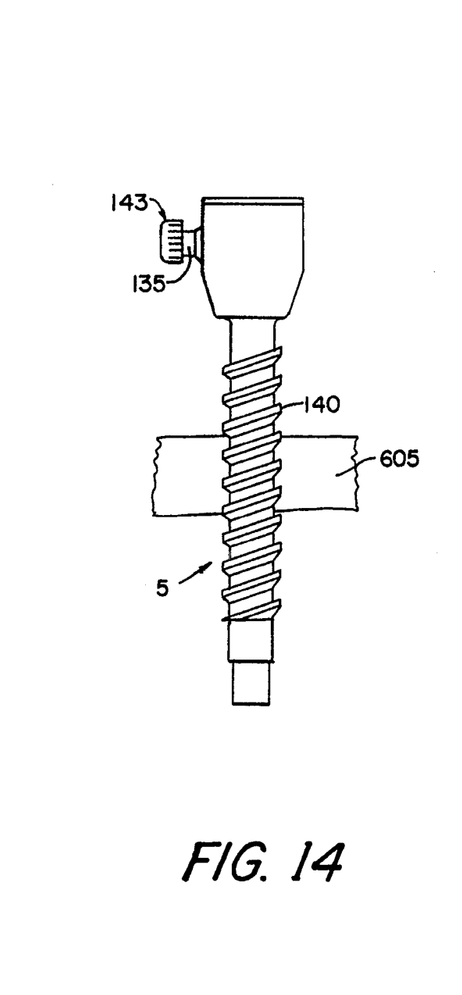
FIG. 14 shows the surgical cannula extending through the abdominal wall of a patient, after the trocar has been removed from the cannula.

Next, trocar 500 is removed from cannula 5 and the cannula is screwed down through abdominal wall 605 using the cannula's helical screw threads 140 until the cannula is securely deployed through abdominal wall 605. See FIG. 14. In this regard it is also to be appreciated that since the distal end 210 of the spring-loaded sleeve 205 will lead the cannula as it is screwed through abdominal wall 605, any inadvertent contact occurring between the advancing cannula and the patient's internal organs can be cushioned by a retreat of sleeve 205 relative to the cannula housing. It is also to be appreciated that as trocar 500 is withdrawn from cannula 5, the second seal member's axial opening 425 (which was extending by the relatively large diameter trocar) will return back to its original size.

At this point in the laparoscopic procedure, the patient's abdomen may already have been inflated with gas. In the event that the patient's abdomen has already been inflated with gas by the time cannula 5 has been placed in the position shown in FIG. 14, it will be appreciated that no gas will be able to leave the abdominal cavity due to the presence of first sealing member 405 across the housing's counterbore 155 (see FIG. 6) and due to the presence of cap 143 on the housing's side extension 135. Alternatively, if desired, the patient's abdomen may now be inflated with gas using cannula 5, if it has not already been previously inflated. More particularly, the cannula's side extension cap 143 is removed, side extension 135 is connected to an appropriate source of suitable gas, and then the gas is introduced into the patient's abdomen via the side extension's bore 170, housing counterbore 150 and sheath passageway 217. Again, it will be appreciated that no gas will be able to exit the proximal end of the cannula due to the presence of first sealing member 405 which normally extends completely across the housing's counterbore 155 and closes off the proximal end of the housing (see FIG. 6).

Cannula 5 may thereafter be used to introduce surgical instruments to the interior surgical site. More particularly, and looking now at FIGS. 15 and 16, a surgical instrument 700 may be passed through cannula 5 so that its distal working end 705 is presented to the surgical site while its proximal grasping end 710 remains outside the body for easy manipulation by the surgeon. It will be appreciated that as surgical instrument 700 is passed through cannula 5, its shaft will first press its way through the snug axial opening 425 in second seal member 410, and then force the first sealing member 405 apart at its slit 420, in the manner shown in FIG. 16. At the same time, however, no gas will be able to leak out of the patient's abdominal cavity through cannula 5 since second sealing member 410 will make a close fit about the shaft of tool 700.

It is not uncommon for a surgical instrument to be moved about laterally and/or axially during use. Cannula 5 is particularly well adapted to accommodate such movement while maintaining a secure seal about the instrument due to the unique construction of the cannula's sealing means 400. More particularly, and looking now at FIGS. 17 and 18, a surgical instrument 700 is shown extending through cannula 5 at an angle to the cannula's longitudinal axis 105. By comparing FIG. 18 with FIG. 16 it will be seen that as instrument 700 moves off the cannula's center axis, the proximal portion 435 and side wall portion 440 of the seal's connecting means 415 deform as necessary so as to permit the second sealing member 410 to follow the instrument. At the same time, however, since second sealing member 410 is a comparatively rigid structure relative to connecting means 415, second sealing member 410 will maintain a snug fit around instrument 700 even as instrument 700 is moved about within the cannula.

Figure 15:
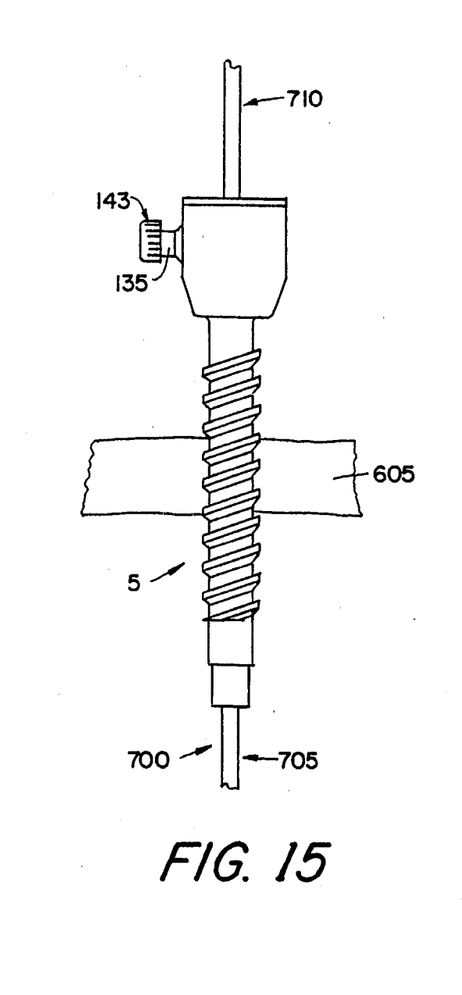
FIGS. 15 and 16 show a surgical instrument extending through the surgical cannula, with the surgical instrument being substantially aligned with the longitudinal axis of the surgical cannula.
Figure 16:
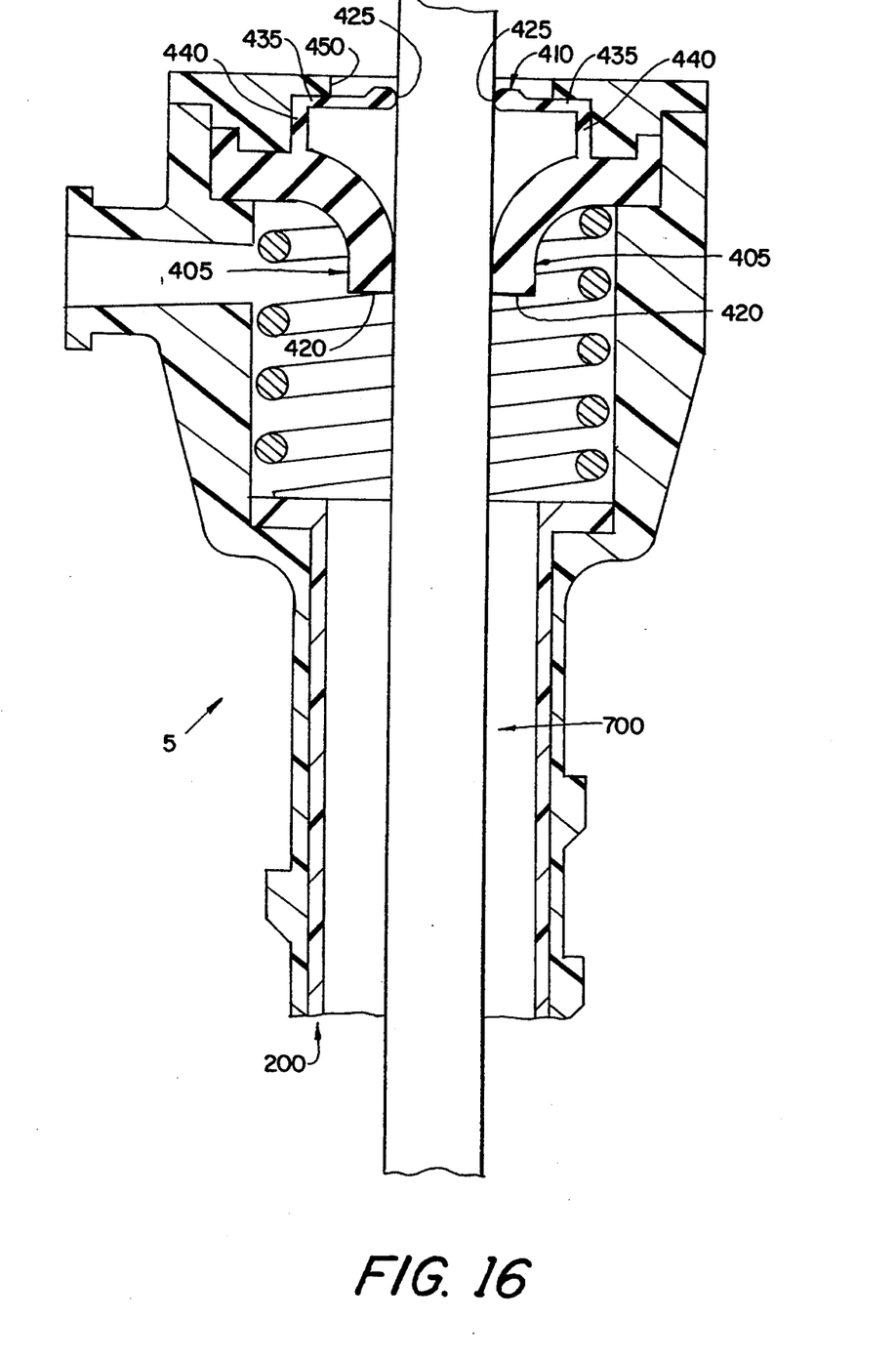
Figure 17:
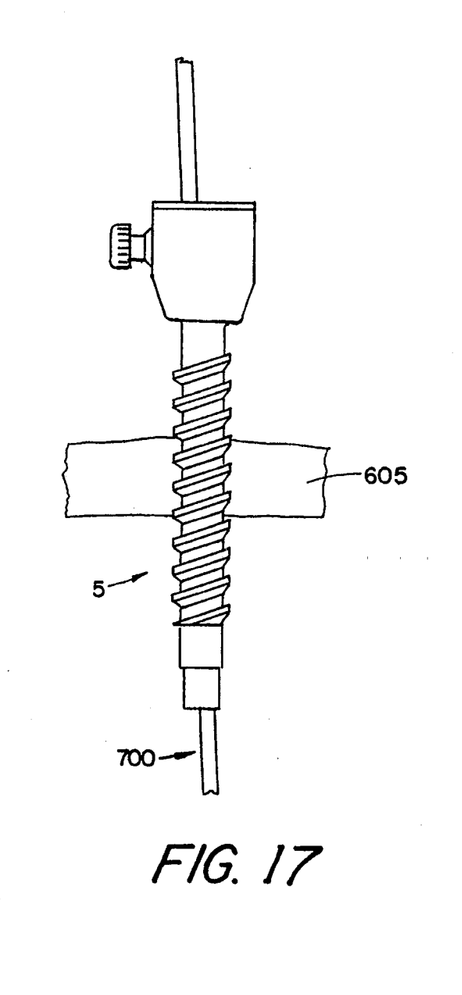
FIGS. 17 and 18 show a surgical instrument extending through the surgical cannula, with the surgical instrument having moved substantially out of alignment with the cannula's longitudinal axis during instrument manipulation.

Subsequently, when instrument 700 returns to axial alignment in the manner shown in FIGS. 15 and 16, the resilient sealing means 400 will also return to the position shown in FIGS. 15 and 16, thereby maintaining a secure seal about the instrument. Finally, when instrument 700 is withdrawn from cannula 5, resilient sealing means 400 will return to the position shown in FIG. 6, whereby first sealing member 405 will once again prohibit gas from passing out the proximal end of the cannula.

Modifications Of The Preferred Embodiment

Numerous modifications may be made to the foregoing preferred embodiment of the invention without departing from the scope of the present invention.

Thus, for example, the first sealing member's slit 420 might be formed with a triangular or cruciform pattern, rather than with a linear pattern as shown.

Furthermore, one might choose to form first sealing member 405, second sealing member 410 and/or connecting means 415 separately from one another.

In addition, it is to be appreciated that the surgical cannula of the present invention could be used in procedures other than laparoscopic procedures, e.g., it could be used in substantially any type of endoscopic procedure where there is need for a cannula of its type. In this respect it is to be appreciated that the term "fluid" as used herein is intended to encompass both gaseous and liquid fluids of the sort encountered in various endoscopic procedures well known in the art.

It is also to be appreciated that in some circumstances one might utilize surgical cannula 5 in conjunction with a surgical obturator, which is a device will known in the art and which is similar to trocar 500 except that it has a blunt distal end in place of sharp point 510.

These and other changes of their type and purpose will be obvious to persons skilled in the art and are considered to be within the scope of the present invention.

Advantages Of The Present Advantage

Numerous advantages are obtained by using the present invention.

For one thing, the present invention provides a novel surgical cannula and trocar system which improves upon surgical cannula and trocar systems of the sort previously known in the art.

For another thing, the present invention provides a novel surgical cannula which provides shield means for protecting operating room personnel from accidental contact with the trocar's sharp tip, wherein the shield means is provided on the surgical cannula and not on the surgical trocar.

Also, the present invention provides a surgical cannula which includes spring-biased means at its distal tip which can act to cushion any accidental contact which might occur with the patient's internal organs during the cannula's deployment or use.

Furthermore, the present invention provides a surgical cannula which has improved sealing means, whereby fluids will be reliably prevented from passing through the cannula both when an instrument extends through the cannula and when no instrument extends through the cannula.

In addition, the present invention provides a surgical cannula which has improved sealing means which is particularly well adapted to sealingly accommodate lateral and axial motion of a surgical instrument extending through the cannula.

Still other advantages associated with the present invention will be obvious to persons skilled in the art.

What is claimed is:

1. Apparatus for use in endoscopic surgery comprising:

a surgical cannula, said surgical cannula comprising an elongate housing, shield means, biasing means, and sealing means;

said elongate housing including a longitudinal axis, a distal end, a proximal end, and an axial passageway extending through said housing from said distal end to said proximal end;

said shield means comprising an elongate tubular sheath having a distal end, a proximal end, and defining an axial passageway extending from said distal end of said sheath to said proximal end of said sheath, said shield means being located in reciprocally slidable relation in said passageway of said housing such that said shield means is movable between (a) a first position in which said distal end of said sheath projects distally from said distal end of said housing, and (b) a second position in which said distal end of said sheath is located substantially within said axial passageway of said housing;

said biasing means being adapted to yieldably urge said sheath into said first position; and said sealing means comprising a first sealing member, a second sealing member, and connecting means connecting said first and second sealing members together in spaced relation to one another, said sealing means extending across said housing passageway such that said first sealing member is disposed toward said distal end of said cannula and said second sealing member is disposed toward said proximal end of said cannula;

said first sealing member comprising a layer of resilient material extending substantially completely across said housing passageway, said layer defining at least one slit extending substantially centrally and axially therethrough so as to form a flap valve configuration;

said second sealing member comprising a resilient structure defining an axial opening and an outer edge, said second sealing member being sized such that the transverse cross-section of said second sealing member is smaller than the transverse cross-section of said sheath passageway; and said connecting means being formed out of a resilient material and comprising a proximal portion connected to said outer edge of said second sealing member and extending outwardly therefrom to a second outer edge, and a side wall portion having an upper edge and a lower edge, said upper edge being connected to said second outer edge of said proximal portion, and said lower edge being connected to said first sealing member, with said side wall portion normally extending substantially vertically between said proximal portion and said first sealing member;

said connecting means being formed so as to be significantly more easily deformable than said second sealing member.

2. Apparatus according to claim 1 wherein said housing passageway comprising a proximally facing shoulder, and said shield means comprises a radially outwardly extending flange adjacent said proximal end of said sheath, said flange being adapted to engage said shoulder when said sheath is in said first position relative to said cannula.

3. Apparatus according to claim 1 further comprising a surgical trocar, said trocar comprising a distal end, a proximal end and at least one cutting edge adjacent said distal end, said trocar being adapted to be received in said housing so that said at least one cutting edge of said trocar will be received within said sheath when said sheath is in its said first position, and further wherein said at least one cutting edge of said trocar will project distally of said housing when said sheath is in its said second position.

4. Apparatus according to claim 1 further comprising a surgical instrument, and wherein said second sealing member and said connecting means are formed such that said instrument may be inserted axially through said axial opening of said second sealing member and form a sealing fit therewith, both when said instrument is aligned with said longitudinal axis of said housing and when said instrument is moved laterally relative to said longitudinal axis of said housing.

5. Sealing means for sealing an opening in a housing, said opening having a distal end and a proximal end, said sealing means comprising a first sealing member, a second sealing member, and connecting means connecting said first and second sealing members together in spaced relation to one another, said sealing means being adapted for location across said opening such that said first sealing member is disposed toward said distal end of said opening and said second sealing member is disposed toward said proximal end of said opening;

said first sealing member comprising a layer of resilient material extending substantially completely across said opening, said layer defining at least one slit extending substantially centrally and axially therethrough so as to form a flap valve configuration;

said second sealing member comprising a resilient structure defining an axial opening and an outer edge, said second sealing member being sized such that the transverse cross-section of said second sealing member is smaller than the transverse cross-section of said opening; and said connecting means being formed out of a resilient material and comprising a proximal portion connected to said outer edge of said second sealing member and extending outwardly therefrom to a second outer edge, and a side wall portion having an upper edge and a lower edge, said upper edge being connected to said second outer edge of said proximal portion, and said lower edge being connected to said first sealing member, with said side wall portion normally extending substantially vertically between said proximal portion and said first sealing member;

said connecting means being formed so as to be significantly more easily deformable than said second sealing member.

6. In a surgical cannula of the sort comprising an elongate housing having a longitudinal axis, a distal end, a proximal end, and an axial passageway extending through said housing from said distal end to said proximal end, and sealing means for preventing the passage of fluid through said passageway while permitting the passage of a surgical instrument through said passageway, the improvement comprising:

said sealing means comprising a first sealing member, a second sealing member, and connecting means connecting said first and second sealing members together in spaced relation to one another, said sealing means extending across said housing passageway such that said first sealing member is disposed toward said distal end of said cannula and said second sealing member is disposed toward said proximal end of said cannula;

said first sealing member comprising a layer of resilient material extending substantially completely across said housing passageway, said layer defining at least one slit extending substantially centrally and axially therethrough so as to form a flap valve configuration;

said second sealing member comprising a resilient structure defining an axial opening and an outer edge, said second sealing member being sized such that the transverse cross-section of said second sealing member is smaller than the transverse cross-section of said housing passageway; and said connecting means being formed out of a resilient material and comprising a proximal portion connected to said outer edge of said second sealing member and extending outwardly therefrom to a second outer edge, and a side wall portion having an upper edge and a lower edge, said upper edge being connected to said second outer edge of said proximal portion, and said lower edge being connected to said first sealing member, with said side wall portion normally extending substantially vertically between said proximal portion and said first sealing member;

said connecting means being formed so as to be significantly more easily deformable than said second sealing member.

7. A method for deploying a surgical cannula in a patient for subsequent use in an endoscopic surgical procedure, said method comprising the steps of:

(a) providing a surgical cannula, said surgical cannula comprising an elongate housing, shield means, biasing means and sealing means;

said elongate housing including a longitudinal axis, a distal end, a proximal end, and an axial passageway extending through said housing from said distal end to said proximal end;

said shield means comprising an elongate tubular sheath having a distal end, a proximal end, and defining an axial passageway extending from said distal end of said sheath to said proximal end of said sheath, said shield means being located in reciprocally slidable relation in said passageway of said housing such that said shield means is movable between (i) a first position in which said distal end of said sheath projects distally from said distal end of said housing, and (ii) a second position in which said axial passageway of said housing;

said biasing means being adapted to yieldably urge said sheath into said first position; and said sealing means being arranged to prevent the passage of fluid through said passageway of said housing while permitting the passageway of a surgical instrument through said passageway of said housing;

said sealing means comprising a first sealing member, a second sealing member, and connecting means connecting said first and second sealing members together in spaced relation to one another, said sealing means extending across said housing passageway such that said first sealing member is disposed toward said distal end of said cannula and said second sealing member is disposed toward said proximal end of said cannula;

said first sealing member comprising a layer of resilient material extending substantially completely across said housing passageway, said layer defining at least one slit extending substantially centrally and axially therethrough so as to form a flap valve configuration;

said second sealing member comprising a resilient structure defining an axial opening and an outer edge, said second sealing member being sized such that the transverse cross-section of said second sealing member is smaller than the transverse cross-section of said sheath passageway; and said connecting means being formed out of a resilient material and comprising a proximal portion connected to said outer edge of said second sealing member and extending outwardly therefrom to a second outer edge, and a side wall portion having an upper edge and a lower edge, said upper edge being connected to said second outer edge of said proximal portion, and said lower edge being connected to said first sealing member, with said side wall portion normally extending substantially vertically between said proximal portion and said first sealing member;

said connecting means being formed so as to be significantly more easily deformable than said second sealing member;

(b) providing a trocar comprising a distal end, a proximal end and at least one cutting edge adjacent said distal end, said trocar being adapted to be received in said housing so that said at least one cutting edge of said trocar will be received within said sheath when said sheath is in its said first position, and further wherein said at least one cutting edge of said trocar will project distally of said housing when said sheath is in its said second position;

(c) inserting said trocar into said housing while said sheath is in its said first position;

(d) placing said distal end of said sheath against said patient adjacent the location where the cannula is to be deployed in said patient; and (e) exerting an axial force on said surgical cannula and trocar so as to cause said sheath to retract into said housing to expose said at least one cutting edge of said trocar and thereafter maintaining said axial force on said surgical cannula and said trocar until said surgical cannula and trocar have been deployed into said patient.

8. A method according to claim 7 further comprising the steps of:

(f) removing said trocar from said housing;

(g) providing a surgical instrument to be used in performing the endoscopic procedure, said surgical instrument having a distal end and a proximal end; and (h) inserting said surgical instrument through said cannula so that said distal end of said instrument is located at the interior surgical site while said proximal end of said instrument is available to be manipulated by the surgeon.

9. In a surgical cannula of the sort comprising an elongate housing having a longitudinal axis, a distal end, a proximal end, and an axial passageway extending through said housing from said distal end to said proximal end, and sealing means for preventing the passage of fluid through said passageway while permitting the passage of a surgical instrument through said passageway, the improvement comprising:

said sealing means comprising a first sealing member and a second sealing member, said first sealing member being disposed in spaced relation to said second sealing member, and said sealing means extending across said housing passageway such that said first sealing member is disposed toward said distal end of said cannula and said second sealing member is disposed toward said proximal end of said cannula;

said first sealing member comprising a layer of resilient material extending substantially completely across said housing passageway, said layer defining at least one slit extending substantially centrally and axially therethrough so as to form a flap valve configuration;

said second sealing member comprising a resilient structure defining an axial opening and an outer edge, said second sealing member being sized such that said second sealing member has a smaller transverse cross-section than the transverse cross-section of said housing passageway;

said second sealing member being maintained in said passageway by connecting means, said connecting means being formed out of a resilient material and comprising a proximal portion connected to said outer edge of said second sealing member and extending outwardly therefrom to a second outer edge, and a side wall portion having an upper edge and a lower edge, said upper edge being connected to said second outer edge of said proximal portion, and said lower edge being connected to said housing by laterally extending support means, and said side wall portion normally extending substantially vertically between said proximal portion and said laterally extending support means, aid connecting means being formed so as to be significantly more easily deformable than said second sealing member, and said second sealing member, said connecting means and said laterally extending support means together forming a fluid impermeable barrier outboard of said axial opening.

* * * * *

UNITED STATES PATENT AND TRADEMARK OFFICE
CERTIFICATE OF CORRECTION

PATENT NO. : 5,380,288
DATED : January 10, 1995
INVENTOR(S) : Rickey D. Hart et al.

It is certified that error appears in the above-indentified patent and that said Letters Patent is hereby corrected as shown below:

Claim 2, column 13, line 19, the word "comprising" should be changed to -- comprises --.

Claim 7, column 15, line 11, before the word "axial", insert the phrase -- distal end of said sheath is located substantially within said --.

Claim 9, column 16, line 63, the word "aid" should be changed to -- said --.

Signed and Sealed this

Eighteenth Day of June, 1996

Attest:

BRUCE LEHMAN

Attesting Officer

Commissioner of Patents and Trademarks